US 7,307,143 B1

(12) United States Patent
Behrens et al.

(10) Patent No.: US 7,307,143 B1
(45) Date of Patent: Dec. 11, 2007

(54) CONDUCTIN PROTEIN AND A RELATED AGENT FOR DIAGNOSING AND TREATING TUMOR ILLNESSES

(75) Inventors: Jürgen Behrens, Berlin (DE); Walter Birchmeier, Schwanebeck (DE)

(73) Assignee: Max-delbrück Institut fur Molekulare Hedizin, Berlin (DE)

( * ) Notice: Subject to any disclaimer, the term of this patent is extended or adjusted under 35 U.S.C. 154(b) by 793 days.

(21) Appl. No.: 09/587,574

(22) Filed: Jun. 5, 2000

Related U.S. Application Data

(63) Continuation of application No. PCT/DE98/02621, filed on Sep. 1, 1998, now abandoned.

(30) Foreign Application Priority Data

Sep. 2, 1997 (DE) ............................... 197 38 205

(51) Int. Cl.
*C07K 14/00* (2006.01)
(52) U.S. Cl. ...................... 530/350; 530/300
(58) Field of Classification Search ................. 530/350

See application file for complete search history.

(56) References Cited

OTHER PUBLICATIONS

Behrens, et al., 1998, Science, vol. 280:596-599.*
Burgess et al., J of Cell Bio. 111:2129-2138, 1990.*
Lazar et al. Molecular and Cellular Biology 8:1247-1252, 1988.*
(Bowie et al. Science, 247:1306-1310, 1990.*
Zeng et al (Jul. 11, 1997, Cell, vol. 90, pp. 181-192).*
Kishida et al (May 1998, J. Biol. Chem. vol. 273, pp. 10823-10826).*
Hitler L. et al., (1997) EMEST11 DATABASE Accession No. AA489748, XP002092738 Siehc das ganze Dokument.
International Search Report for PCT Application No. PCT/DE98/02621.

* cited by examiner

*Primary Examiner*—Misook Yu
(74) *Attorney, Agent, or Firm*—Goodwin Procter, LLP.

(57) ABSTRACT

The invention relates to a new method for combating tumor illnesses through the use of molecular biological associations during formation of the tumor. The aim of the invention is to develop a method for controlling the regulation of β-catenine in body cells. The object of the invention is a new protein which bonds to β-catenine and the subsequent cytoplasmic decomposition of said protein. This protein has the amino-acid sequence according to FIG. 1 and is designated as conductine. Agents for diagnosing and treating tumor illnesses are developed from the occurrence and the action of conductine in body cells.

5 Claims, 10 Drawing Sheets

```
MSSAVLVTLLPDPSSSFREDAPRPPVPGEEGETPPCQPSVGKVQSTKPMPVSSNARRNED    60
GLGEPEGRASPDSPLTRWTKSLHSLLGDQDGAYLFRTFLEREKCVDTLDFWFACNGFRQM  120
NLKDTKTLRVAKAIYKRYIENNSVVSKQLKPATKTYIRDGIKKQQIGSVMFDQAQTEIQA  180
VMEENAYQVFLTSDIYLEYVRSGGENTAYMSNGGLGSLKVLCGYLPTLNEEEEWTCADLK  240
CKLSPTVVGLSSKTLRATASVRSTETAENGFRSFKRSDPVNPYHVGSGYVFAPATSANDS  300
ELSSDALTDDSMSMTDSSVDGVPPYRMGSKKQLQREMHRSVKANGQVSLPHFPRTHRLPK  360
EMTPVEPAAFAAELISRLEKLKLELESRHSLEERLQQIREDEEKEGSEQALSSRDGAPVQ  420
HPLALLPSGSYEEDPQTILDDHLSRVLKTPGCQSPGVGRYSPRSRSPDHHHQHHHQQCH  480
TLLSTGGKLPPVAACPLLGGKSFLTKQTTKHVHHHYIHHHAVPKTKEEIEAEATQRVRCL  540
CPGGTDYYCYSKCKSHPKAPEPLPGEQFCGSRGGTLPKRNAKGTEPGLALSARDGGMSSA  600
AGGPQLPGEEGDRSQDVWQWMLESERQSKSKPHSAQSIRKSYPLESARAAPGERVSRHHL  660
LGASGHSRSVARAHPFTQDPAMPPLTPPNTLAQLEEACRRLAEVSKPQKQRCCVASQQRD  720
PNHSAAGQAGASPFANPSLAPEDHKEPKKLASVHALQASELVVTYFFCGEEIPYRRMLKA  780
QSLTLGHFKEQLSKKGNYRYYFKKASDEFACGAVFEEIWDDETVLPMYEGRILGKVERID  840
```

```
MSSAVLVTLLPDPSSSFREDAPRPPVPGEEGETPPCQPSVGKVQSTKPMPVSSNARRNED   60
GLGEPEGRASPDSPLTRWTKSLHSLLGDQDGAYLFRTFLEREKCVDTLDFWFACNGFRQM  120
NLKDTKTLRVAKAIYKRYIENNSVVSKQLKPATKTYIRDGIKKQQIGSVMFDQAQTEIQA  180
VMEENAYQVFLTSDIYLEYVRSGGENTAYMSNGGLGSLKVLCGYLPTLNEEEEWTCADLK  240
CKLSPTVVGLSSKTLRATASVRSTETAENGFRSFKRSDPVNPYHVGSGYVFAPATSANDS  300
ELSSDALTDDSMSMTDSSVDGVPPYRMGSKKQLQREMHRSVKANGQVSLPFFPRTHRLPK  360
EMTPVEPAAFAAELISRLEKLKLELESRHSLEERLQQIPEDEEKEGSEQALSSRDGAPVQ  420
HPLALLPSGSYEEDPQTILDDHLSRVLKTPGCQSPGVGRYSPRSRSPDHHQHHHHQQCH  480
TLLSTGGKLPPVAACPLLGGKSFLTKQTTKHVHHHYIHHHAVPKTKEEIEAEATQRVRCL  540
CPGGTDYYCYSKCKSHPKAPEPLPGEQFCGSRGGTLPKRNAKGTEPGLALSARDGGMSSA  600
AGGPQLPGEEGDRSQDVWQWMLESERQSKSKPHSAQSIRKSYPLESARAAPGERVSRHHL  660
LGASGHSRSVARAHPFTQDPAMPPLTPPNTLAQLEEACRRLAEVSKPQKQRCCVASQQRD  720
PAHSAAGQAGASPFANPSLAPEDHKEPKKLASVHALQASELVVTYFFCGEEIPYRPMLKA  780
QSLTLGHFKEQLSKKGNYRYYFKKASDEFACGAVFEEIWDDETVLPMYEGRILGKVERID  840
```

FIG. 1

```
CAGCCCGTTCGCGATGGATTTCGGGGCCACCCGGAGGCCGAGGCGTCCGGCTCCCCAAAGG    60
AGAGCTTTGCTGTAAAAGAGAGGAGGCTCACATGAGCCCCTGCTGACTTAAGAGAGACCA   120
AGCCGATTGCTGAGAGGAACTGGAAGAAGAAAAAGGAGGAGGAGGGAAAAAAAGCAAAAC   180
AAAATCCAAACTCAGTGAGACGCTCTCCCTCACCATGAGTAGCGCCGTGTTAGTGACTCT   240
CCTTCCAGATCCCAGCAGCAGCTTCCGCGAGGATGCTCCGCGGCCCCCGGTTCCGGGAGA   300
AGAAGGGGAGACCCCACCGTGTCAGCCTAGTGTGGGCAAGGTCCAGTCCACCAAACCTAT   360
GCCCGTTTCCTCTAATGCTAGGCGGAATGAAGATGGACTGGGGGAGCCCGAGGGGCGGGC   420
CTCCCCCGATTCCCCTTTGACCAGGTGGACCAAGTCTTTACACTCCTTGTTGGGTGACCA   480
GGATGGTGCATACCTCTTCCGGACTTTCCTGGAGAGGGAGAAATGTGTGATACGCTGGA    540
CTTCTGGTTTGCTTGTAATGGGTTCAGGCAGATGAACCTGAAGGATACCAAAACTTTGCG   600
AGTGGCCAAAGCAATCTATAAGAGGTACATTGAGAACAACAGCGTTGTCTCCAAGCAGCT   660
GAAGCCCGCCACCAAGAGCTACATACGAGATGGCATCAAGAAGCAACAGATCGGCTCGGT   720
CATGTTTGACCAGGCACAGACCGAGATCCAGGCAGTGATGGAGGAAAATGCCTACCAGGT   780
GTTCTTGACTTCTGACATTTACCTGGAATATGTGAGGAGTGGGGGGAAAACACAGCTTA    840
CATGAGTAACGGGGACTGGGGAGCCTAAAGGTCTTATGTGGCTACCTCCCCACCTTGAA    900
TGAAGAAGAGGAGTGGACGTGTGCCGACCTCAAGTGCAAACTCTCACCCACCGTGGTTGG   960
CTTGTCCAGCAAAACTCTTCGGGCCACCGCGAGTGTGAGATCCACGGAAACAGCTGAAAA  1020
CGGATTCAGGTCCTTCAAGAGAAGCGACCCAGTCAATCCTTATCACGTAGGTTCCGGCTA  1080
TGTCTTTGCACCAGCCACCAGCGCCAACGACAGCGAGTTATCCAGCGACGCACTGACCGA  1140
CGATTCCATGTCCATGACGGACAGTAGCGTAGATGGAGTCCCTCCTTACCGCATGGGGAG  1200
TAAGAAACAGCTCCAGAGAGAGATGCATCGCAGTGTGAAGGCCAATGCCCAAGTGTCTCT  1260
ACCTCATTTTCCGAGAACCCACCGCCTGCCCAAGGAGATGACGCCTGTGGAACCTGCTGC  1320
CTTCGCCGCCGAGCTCATCTCCAGGCTGGAGAAACTGAAACTGGAGCTGGAAAGCCGCCA  1380
TAGTCTGGAGGAGCGGCTGCAGCAGATCCGGGAGGATGAAGAAAAGGAGGGGTCTGAGCA  1440
GGCCCTGAGCTCACGGGATGGAGCACCGGTCCAGCACCCCCTGGGCCTCCTACCCTCCGG  1500
CAGCTATGAAGAGGACCCACAAACCATTTTGGACGACCACCTCTCCAGGGTCCTCAAGAC  1560
CCCCGGCTGTCAATCCCTGGTGTGGGTCGCTACAGCCCACGGTCCCGCTCCCCGACCA    1620
CCACCACCAGCACCACCACCATCAGCAGTGTCATACCCTTCTTTCGACTGGGGGCAAGCT  1680
GCCCCCCGTGGCTGCTTGCCCCCTCCTTGGAGGGCAAGAGCTTCCTGACCAAACAGAGGAC 1740
GAAGCACGTTCACCACCACTACATCCACCACCACGCCGTCCCCAAGACCAAGGAGGAGAT  1800
CGAGGCAGAAGCCACACAGAGAGTCCGCTGCCTCTGTCCTGGGGGAACAGATTATTATTG  1860
CTACTCCAAATGCAAAAGCCACCCGAAGGCTCCAGAGCCCCTGCCTGGGGAGCAGTTTTG  1920
TGGCAGCAGAGGTGGTACCTTGCCAAAACGGAATGCAAAGGGCACCGAACCGGGTCTTGC  1980
ACTGTCGGCCAGGGATGGAGGGATGTCCAGTGCAGCGGGGGGCCCCAGCTTGCTGGGGA   2040
AGAAGGAGACCGGTCACAGGATGTCTGGCAGTGGATGTTGGAGAGTGAGCGGCAGAGCAA  2100
GTCCAAGCCCCATAGTGCCCAAAGCATAAGAAAGAGCTACCCATTGGAGTCTGCCCGTGC  2160
GGCCCCAGGAGAACGAGTCAGCCGGCACCATCTGTTGGGGGCCAGCGGACACTCCCGCTC  2220
AGTGGCCCGGGCTCACCCATTTACCCAGGACCCTGCAATGCCTCCCCTTACCCCACCCAA  2280
CACTTTGGCACAGCTAGAGGAAGCCTGCCGCCAGGCTGGCAGAGGTGTCGAAGCCCCAGAA 2340
GCAGCGGTGCTGCGTGGCCAGTCAGCAGAGGGACAGGAACCACTCGGCTGCTGGTCAGGC  2400
AGGAGCCTCACCCTTCGCCAACCCAAGCCTGGCTCCAGAAGATCACAAAGAGCCAAAGAA  2460
ACTGGCAAGTGTCCACGCGCTCCAGGCCAGTGAGCTGGTTGTCACCTACTTTTTCTGTGG  2520
AGAAGAAATTCCATACAGGAGGATGCTGAAGGCTCAAAGCTTGACCCTGGGCCACTTCAA  2580
GGAGCAGCTCAGCAAAAAGGGAAATTACAGGTATTATTTCAAGAAGGCGAGTGACGAATT  2640
TGCCTGCGGAGCAGTTTTTGAGGAGATCTGGGACGACGAGACAGTGCTCCCCATGTACGA  2700
AGGCAGGATCCTGGGCAAAGTGGAGAGGATCGACTGAGCCTTGGCCTCCTCGGCGTGCAA  2760
CCTGGGCAAGCACCTCGGCGTGCACCATGGAGCCGAAGCCCAGAGACCCTGTCTCAGGCC  2820
TACGC 2825
```

FIG. 2

```
215 ATG AGT AGC GCC GTG TTA GTG ACT
  1  M   S   S   A   V   L   V   T

CTC CTT CCA GAT CCC AGC AGC AGC TTC
 L   L   P   D   P   S   S   S   F

CGC GAG GAT GCT CCG CGG CCC CCG GTT
 R   E   D   A   P   R   P   P   V

CCG GGA GAA GAA GGG GAG ACC CCA CCG
 P   G   E   E   G   E   T   P   P

TGT CAG CCT AGT GTG GGC AAG GTC CAG
 C   Q   P   S   V   G   K   V   Q

TCC ACC AAA CCT ATG CCC GTT TCC TCT
 S   T   K   P   M   P   V   S   S

AAT GCT AGG CGG AAT GAA GAT GGA CTG
 N   A   R   R   N   E   D   G   L

GGG GAG CCC GAG GGG CGG GCC TCC CCC
 G   E   P   E   G   R   A   S   P

GAT TCC CCT TTG ACC AGG TGG ACC AAG
 D   S   P   L   T   R   W   T   K

TCT TTA CAC TCC TTG TTG GGT GAC CAG
 S   L   H   S   L   L   G   D   Q

GAT GGT GCA TAC CTC TTC CGG ACT TTC
 D   G   A   Y   L   F   R   T   F

CTG GAG AGG GAG AAA TGT GTG GAT ACG
 L   E   R   E   K   C   V   D   T

CTG GAC TTC TGG TTT GCT TGT AAT GGG
 L   D   F   W   F   A   C   N   G
```

FIG. 3A

```
TTC AGG CAG ATG AAC CTG AAG GAT ACC
 F   R   Q   M   N   L   K   D   T

AAA ACT TTG CGA GTG GCC AAA GCA ATC
 K   T   L   R   V   A   K   A   I

TAT AAG AGG TAC ATT GAG AAC AAC AGC
 Y   K   R   Y   I   E   N   N   S

GTT GTC TCC AAG CAG CTG AAG CCC GCC
 V   V   S   K   Q   L   K   P   A

ACC AAG ACC TAC ATA CGA GAT GGC ATC
 T   K   T   Y   I   R   D   G   I

AAG AAG CAA CAG ATC GGC TCG GTC ATG
 K   K   Q   Q   I   G   S   V   M

TTT GAC CAG GCA CAG ACC GAG ATC CAG
 F   D   Q   A   Q   T   E   I   Q

GCA GTG ATG GAG GAA AAT GCC TAC CAG
 A   V   M   E   E   N   A   Y   Q

GTG TTC TTG ACT TCT GAC ATT TAC CTG
 V   F   L   T   S   D   I   Y   L

GAA TAT GTG AGG AGT GGG GGG GAA AAC
 E   Y   V   R   S   G   G   E   N

ACA GCT TAC ATG AGT AAC GGG GGA CTG
 T   A   Y   M   S   N   G   G   L

GGG AGC CTA AAG GTC TTA TGT GGC TAC
 G   S   L   K   V   L   C   G   Y

CTC CCC ACC TTG AAT GAA GAA GAG GAG
 L   P   T   L   N   E   E   E   E
```

FIG. 3B

```
TGG ACG TGT GCC GAC CTC AAG TGC AAA
 W   T   C   A   D   L   K   C   K

CTC TCA CCC ACC GTG GTT GGC TTG TCC
 L   S   P   T   V   V   G   L   S

AGC AAA ACT CTT CGG GCC ACC GCG AGT
 S   K   T   L   R   A   T   A   S

GTG AGA TCC ACG GAA ACA GCT GAA AAC
 V   R   S   T   E   T   A   E   N

GGA TTC AGG TCC TTC AAG AGA AGC GAC
 G   F   R   S   F   K   R   S   D

CCA GTC AAT CCT TAT CAC GTA GGT TCC
 P   V   N   P   Y   H   V   G   S

GGC TAT GTC TTT GCA CCA GCC ACC AGC
 G   Y   V   F   A   P   A   T   S

GCC AAC GAC AGC GAG TTA TCC AGC GAC
 A   N   D   S   E   L   S   S   D

GCA CTG ACC GAC GAT TCC ATG TCC ATG
 A   L   T   D   D   S   M   S   M

ACG GAC AGT AGC GTA GAT GGA GTC CCT
 T   D   S   S   V   D   G   V   P

CCT TAC CGC ATG GGG AGT AAG AAA CAG
 P   Y   R   M   G   S   K   K   Q

CTC CAG AGA GAG ATG CAT CGC AGT GTG
 L   Q   R   E   M   H   R   S   V

AAG GCC AAT GGC CAA GTG TCT CTA CCT
 K   A   N   G   Q   V   S   L   P

CAT TTT CCG AGA ACC CAC CGC CTG CCC
 H   F   P   R   T   H   R   L   P
```

FIG. 3C

```
AAG GAG ATG ACG CCT GTG GAA CCT GCT
 K   E   M   T   P   V   E   P   A

GCC TTC GCC GCC GAG CTC ATC TCC AGG
 A   F   A   A   E   L   I   S   R

CTG GAG AAA CTG AAA CTG GAG CTG GAA
 L   E   K   L   K   L   E   L   E

AGC CGC CAT AGT CTG GAG GAG CGG CTG
 S   R   H   S   L   E   E   R   L

CAG CAG ATC CGG GAG GAT GAA GAA AAG
 Q   Q   I   R   E   D   E   E   K

GAG GGG TCT GAG CAG GCC CTG AGC TCA
 E   G   S   E   Q   A   L   S   S

CGG GAT GGA GCA CCG GTC CAG CAC CCC
 R   D   G   A   P   V   Q   H   P

CTG GCC CTC CTA CCC TCC GGC AGC TAT
 L   A   L   L   P   S   G   S   Y

GAA GAG GAC CCA CAA ACC ATT TTG GAC
 E   E   D   P   Q   T   I   L   D

GAC CAC CTC TCC AGG GTC CTC AAG ACC
 D   H   L   S   R   V   L   K   T

CCC GGC TGT CAA TCC CCT GGT GTG GGT
 P   G   C   Q   S   P   G   V   G

CGC TAC AGC CCA CGG TCC CGC TCC CCC
 R   Y   S   P   R   S   R   S   P

GAC CAC CAC CAC CAG CAC CAC CAC CAT
 D   H   H   H   Q   H   H   H   H
```

FIG. 3D

```
CAG CAG TGT CAT ACC CTT CTT TCG ACT
 Q   Q   C   H   T   L   L   S   T

GGG GGC AAG CTG CCC CCC GTG GCT GCT
 G   G   K   L   P   P   V   A   A

TGC CCC CTC CTT GGA GGC AAG AGC TTC
 C   P   L   L   G   G   K   S   F

CTG ACC AAA CAG ACG ACG AAG CAC GTT
 L   T   K   Q   T   T   K   H   V

CAC CAC CAC TAC ATC CAC CAC CAC GCC
 H   H   H   Y   I   H   H   H   A

GTC CCC AAG ACC AAG GAG GAG ATC GAG
 V   P   K   T   K   E   E   I   E

GCA GAA GCC ACA CAG AGA GTC CGC TGC
 A   E   A   T   Q   R   V   R   C

CTC TGT CCT GGG GGA ACA GAT TAT TAT
 L   C   P   G   G   T   D   Y   Y

TGC TAC TCC AAA TGC AAA AGC CAC CCG
 C   Y   S   K   C   K   S   H   P

AAG GCT CCA GAG CCC CTG CCT GGG GAG
 K   A   P   E   P   L   P   G   E

CAG TTT TGT GGC AGC AGA GGT GGT ACC
 Q   F   C   G   S   R   G   G   T

TTG CCA AAA CGG AAT GCA AAG GGC ACC
 L   P   K   R   N   A   K   G   T

GAA CCG GGT CTT GCA CTG TCG GCC AGG
 E   P   G   L   A   L   S   A   R

GAT GGA GGG ATG TCC AGT GCA GCG GGG
 D   G   G   M   S   S   A   A   G
```

FIG. 3E

```
GGC CCC CAG CTT CCT GGG GAA GAA GGA
 G   P   Q   L   P   G   E   E   G

GAC CGG TCA CAG GAT GTC TGG CAG TGG
 D   R   S   Q   D   V   W   Q   W

ATG TTG GAG AGT GAG CGG CAG AGC AAG
 M   L   E   S   E   R   Q   S   K

TCC AAG CCC CAT AGT GCC CAA AGC ATA
 S   K   P   H   S   A   Q   S   I

AGA AAG AGC TAC CCA TTG GAG TCT GCC
 R   K   S   Y   P   L   E   S   A

CGT GCG GCC CCA GGA GAA CGA GTC AGC
 R   A   A   P   G   E   R   V   S

CGG CAC CAT CTG TTG GGG GCC AGC GGA
 R   H   H   L   L   G   A   S   G

CAC TCC CGC TCA GTG GCC CGG GCT CAC
 H   S   R   S   V   A   R   A   H

CCA TTT ACC CAG GAC CCT GCA ATG CCT
 P   F   T   Q   D   P   A   M   P

CCC CTT ACC CCA CCC AAC ACT TTG GCA
 P   L   T   P   P   N   T   L   A

CAG CTA GAG GAA GCC TGC CGC AGG CTG
 Q   L   E   E   A   C   R   R   L

GCA GAG GTG TCG AAG CCC CAG AAG CAG
 A   E   V   S   K   P   Q   K   Q

CGG TGC TGC GTG GCC AGT CAG CAG AGG
 R   C   C   V   A   S   Q   Q   R
```

FIG. 3F

```
GAC AGG AAC CAC TCG GCT GCT GGT CAG
 D   R   N   H   S   A   A   G   Q

GCA GGA GCC TCA CCC TTC GCC AAC CCA
 A   G   A   S   P   F   A   N   P

AGC CTG GCT CCA GAA GAT CAC AAA GAG
 S   L   A   P   E   D   H   K   E

CCA AAG AAA CTG GCA AGT GTC CAC GCG
 P   K   K   L   A   S   V   H   A

CTC CAG GCC AGT GAG CTG GTT GTC ACC
 L   Q   A   S   E   L   V   V   T

TAC TTT TTC TGT GGA GAA GAA ATT CCA
 Y   F   F   C   G   E   E   I   P

TAC AGG AGG ATG CTG AAG GCT CAA AGC
 Y   R   R   M   L   K   A   Q   S

TTG ACC CTG GGC CAC TTC AAG GAG CAG
 L   T   L   G   H   F   K   E   Q

CTC AGC AAA AAG GGA AAT TAC AGG TAT
 L   S   K   K   G   N   Y   R   Y

TAT TTC AAG AAG GCG AGT GAC GAA TTT
 Y   F   K   K   A   S   D   E   F

GCC TGC GGA GCA GTT TTT GAG GAG ATC
 A   C   G   A   V   F   E   E   I

TGG GAC GAC GAG ACA GTG CTC CCC ATG
 W   D   D   E   T   V   L   P   M

TAC GAA GGC AGG ATC CTG GGC AAA GTG
 Y   E   G   R   I   L   G   K   V

GAG AGG ATC GAC TGA 2737
 E   R   I   D  Stop
```

FIG. 3G

CONDUCTIN PROTEIN AND A RELATED AGENT FOR DIAGNOSING AND TREATING TUMOR ILLNESSES

This application is a continuation of International Patent Application No. PCT/DE98/02621, filed Sep. 1, 1998, now abandoned.

FIELD OF THE INVENTION

The invention relates to a new way of combating tumor diseases by utilizing molecular biological relationships of the formation of tumors. In particular, it relates to a new agent for diagnosing tumor diseases and a material based as the new agent for the treatment of such diseases. The invention also relates to the new protein conductin, its mutants and variations as well as to parts thereof, to the analogous cDNA sequences and to their use in the gene-therapy and pharmacological methods.

BACKGROUND

Cadherines and catenines form cell adhesion complexes, which are responsible in numerous tissues for the adhesion of cells to one another. The cadherines are trans-membrane proteins and produce the direct contact between adjacent cells. α-, β- and γ-catenine are cytoplasmic components, which connect the cadherines with the actin cytoskeleton. Aside from their function in cell adhesion, the catenines also play a decisive role in signal transduction processes. β-Catenine in vertebrates and the homologous, segment polarity gene product, armadillo in drosophila, are stabilized by the Wnt/wingless signal path (Nusse, R., Cell 89, 321–323, 1997). This leads to an increase in the cytoplasmic fraction of these proteins, which is not bound to cadherine, which thereupon could interact with HMG transcription factors of the LEF-1/TCF families. As a result, β-catenine/armadillo is transported into the cell nucleus where, together with the LEF/TCF proteins, it binds to the DNA and activates certain genes (Behrens, J. et al., Nature 382, 638–642, 1996).

This signal path also plays an important role in the formation of tumors. In epithelial cells of the colon, the cytoplasmic pool of β-catenine is strictly regulated by the tumor suppressor gene product APC (Adenomatosis Polyposis Coli). Mutations of APC, such as those occurring in 80% of all colon cancers, lead to shortened forms of the APC protein, which are no longer able to destabilize β-catenine. As a result, permanent complexes of β-catenine with the HMG transcription factor TCF-4, which are asserted to be responsible for the transformation of the cells, are found in these tumors. This theory is supported by the recent finding that, in tumors in which APC is not changed, mutations of β-catenine occur. These also lead to cytoplasmic stabilization of β-catenine and to an association with LEF-1/TCF factors (Morin, P. J. et al., Science 275, 1787–1790).

BRIEF DESCRIPTION OF THE DRAWING

The invention is disclosed below with reference being had to the drawing, wherein FIG. 1 is the amino acid sequence 1 to 840 of Conductine (SEQ ID NO: 1);

FIG. 2 is the nucleotide sequence of Conductine (SEQ ID NO: 6);

FIG. 3 is the gene comparison sequence (SEQ ID NO: 1) and the nucleotide sequence (nucleotide #251 to #2737 of SEQ ID: 6)

DESCRIPTION OF THE INVENTION

Figure 4:
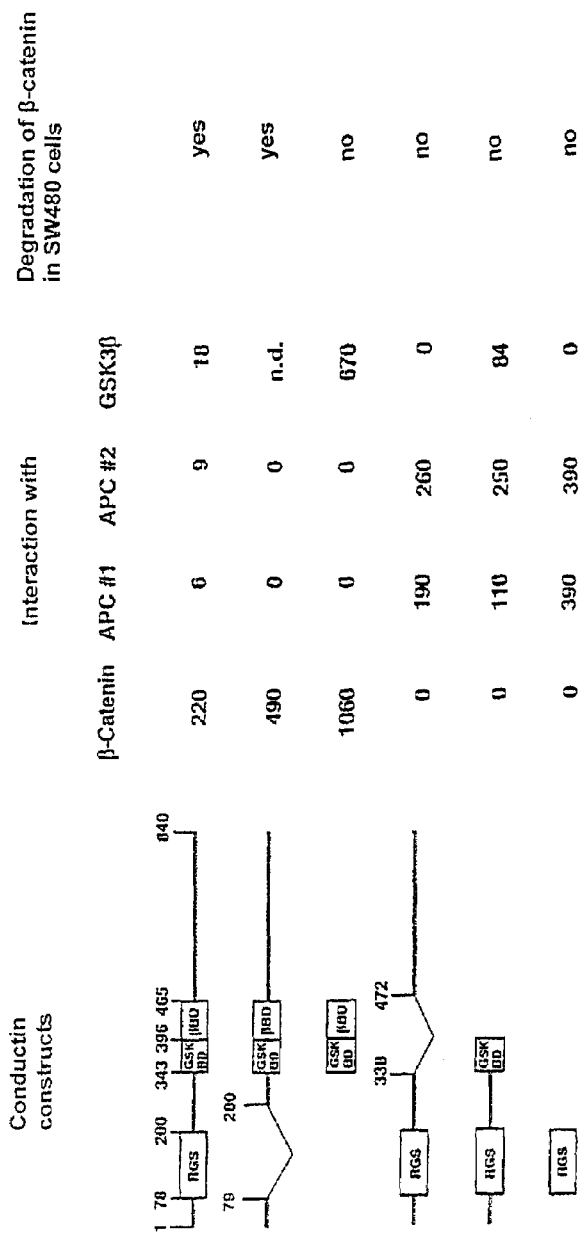
FIG. 4 is a showing of of interaction stuidies in the 2-hybrid system.

It is an object of the present invention to find a new way to prevent the formation of tumors. It is based on the objective of finding a method for controlling the regulation of β-catenine in cells of the body.

It is an object of the present invention to identify a new protein which binds to β-catenine and leads to its cytoplasmic breakdown. This protein has the amino acid sequence shown in FIG. 1 and we gave it the name conductin.

The invention is based on our realization that conductin binds to APC fragments over a β-catenine binding domain at β-catenine, over a glycogen synthase kinase 3β (GSK 3b) binding domain at GSK 3b and over a so-called domain signaling regulator of G-protein (RGS) which is a part of conductin and interacts with the tumor suppressor protein APC. As a result, there is cytoplasmic degradation of β-catenine and in vertebrates, blockage of the Wnt/wingless signal path. That establishes that conductine is an important regulator of the β-catenine function and in interaction with APC contributes to the suppression of tumors.

Thus the invention relates to a material for diagnosing tumor diseases, which is characterized by the presence and the amount of conductine, its mutants and variations or its parts detected in cells of the body. This detection can be carried out on the protein level with specific antibodies, particularly with monoclonal antibodies.

Pursuant to the present invention, the diagnosis of tumor diseases can also be carried out on the gene level. For this purpose, the gene, which codes for conductine, its mutants and variations or parts thereof and/or mRNA sequences, which are read by these genes, are detected with selected oligonucleotide primers and cDNA probes, which are derived from the gene sequence of the conductine and mutations.

The material of the present invention for the treatment of tumor diseases contains substances which activate/reactivate the action of conductin in the body. Above all, these are materials, which activate the gene promoter of conductin or materials, which increase the stability of the mRNA sequences derived from the conductin genes. Pursuant to the invention, the main objective of all of these materials to increase the activity of the conductin in the cells of the body. For this purpose, for example, low molecular weight substances, come into consideration, which are found, for example, by high throughput number screening. High throughput screening can be performed by analyzing low molecular weight substances for their ability to stimulate the activity of the conductin promoter or the expression of the conductin mRNA protein after treatment of cultured cells. Alternatively, substances can be screened for active phospharylation of β-catenine by conductin in in vitro kinase reactions.

The present invention also includes gene therapeutic materials, containing genes, which code for conductin, its mutants and variations or parts thereof, or mRNA sequences, which are read by these genes.

Furthermore, the new protein conductin of FIG. 1—SEQ ID No. 1 its mutants and variations, as well as parts thereof are a part of the present invention. Especially suitable partial sequences are the amino acids 78 to 200 (RGS)—SEQ ID No. 2, 343–396 (GSK 3b-binding domains)—SEQ ID. No.

3, 397–465 (b-catenine binding domains)—SEQ ID No. 4 and 783–833 (disheveled homology region)—SEQ ID No. 5. Partial sequences of the Adenomatosis Poliposis Coli (APC), which are characterized by the amino acid sequences 1464–1604, 1516–1595, 1690–1778 and 1995–2083 as RGS-domain interaction sites, are also part of the extent of the invention, as are also the analogous cDNA sequences, especially the full cDNA sequence of the conductin (base pairs 1–2825) of FIG. 2—SEQ ID No. 6, as well as the partial sequences of the conductin of the nucleotide sequence 446–814 (RGS gene section)—SEQ ID No. 7, of the nucleotide sequence 1241–1402 (gene section of GSK 3b-binding domains)—SEQ ID No. 8, 1403–1609 (gene section of the β-catenine binding domains)—SEQ ID No. 9 and of the nucleotide sequence 2561–2713 (gene section of the disheveled homology region)—SEQ ID No. 10.

The present invention also relates to a gene therapy process for tumor diseases, which comprises constructing a vector with the conductine gene and restoring conductine in cells of a patient in need therefor by carrying out a gene transfer in the body of the patient The invention is explained in greater detail by reference to the following examples.

Conductin was identified by a yeast 2-hybrid screen as a β-catenine interaction partner. The complete cDNA sequence was subsequently isolated and sequenced. The derived amino acid sequence of conductin is shown in FIG. 1. The nucleotide sequence is shown in FIG. 2 at Position 1–2825 and the gene comparison of the amino acid sequence and the nucleotide sequence is shown in FIG. 3 with the sequence regions marked as in FIG. 1. The conductin cDNA codes a protein of 840 amino acids and has a calculated molecular weight of 92.8 kDa. The RGS domains (shown in double underlining), the β-catenine binding domains (shown in simple underling), and the disheveled homology region (bold letters) are emphasized. By a comparison of sequences, an RGS domain (amino acid 78–200) and a domain (amino acid 783–833, disheveled homology region), related to the protein disheveled, were identified (FIGS. 1–3). The GSK 3b- and β-catenine binding domains (amino acids 343–396 to 397–465) were discovered by interaction studies in the 2-hybrid system (FIG. 4). It was observed that these domains are sufficient and necessary for the binding to GSK 3b or to β-catenine (FIG. 4). The conductine protein and derived partial pieces are shown diagrammatically. The RGS domains (RGS), the GSK 3b-binding domains (GSK BD) and the β-catenine binding sites (b-BD) are emphasized. The interaction with β-catenine with the APC fragments of amino acids 1464–1604 (APCfr. 1) and 1516–1595 (APCfr. 2) and GSK 3b were investigated in the yeast 2-hybrid assay and quantified as β-galactosidase units. It can be seen that the binding of the β-catenine to the β-catenine binding site is limited; the other parts of the protein do not contribute to this. The analysis furthermore shows the exclusive interaction of APC with the RGS domains of conductin. Comparable results for the binding to the RGS domains were obtained with the APC fragments of amino acids 1690–1778 and 1995–2083. The breakdown of β-catenine into SW480 cells by conductin was analyzed after transient expression of the given proteins and immunofluorescence staining of β-catenine. Only partial pieces of conductin, which bind to β-catenine, lead to this breakdown. The analysis finally shows the binding of GSK 3b to the GSK 3b-binding domains of conductin. On the other hand, the RGS homology region and the disheveled homology region do not participate. The interaction of conductine with GSK 3b and β-catenine was also biochemically confirmed in co-immunoprecipitation experiments.

The effect of conductin on β-catenine was investigated in SW480 cells. In these cells, the tumor suppressor gene product APC is mutated, as a result of which there is an increase in the cytoplasmic and especially in the nuclear content of β-catenine. The introduction of conductin into these cells leads to a drastic breakdown of β-catenin, as a result of which the cells are depleted of cytoplasmic β-catenine and of β-catenine in the cell nucleus (FIG. 4). This effect on the content of β-catenine is equal in intensity to that of not-mutated APC, from which it can be concluded that conductin also acts as a tumor suppressor by regulating β-catenin. Moreover, it was shown that conductin also inhibits the Wnt/wingless signal path in Xenopus embryos due to its effect on b-catenine. Wnt/wingless are secreted proteins that counteract conductin function in various tissues.

It was also noted that conductin interacts directly with APC. APC fragments of amino acids 1464–1604, 1516–1595, 1690–1778 and 1995–2083 were identified as interaction sites for conductin. In conductin, the binding to APC takes place over the RGS domains, this region is sufficient and necessary for the interaction. The other domains in conductin do not participate (FIG. 4).

The invention claimed is:

1. An isolated polypeptide comprising the amino acid sequence of SEQ ID NO: 1.

2. An isolated polypeptide consisting of the amino acid sequence of SEQ ID NO: 2.

3. An isolated polypeptide consisting of the amino acid sequence of SEQ ID NO: 3.

4. An isolated polypeptide consisting of the amino acid sequence of SEQ ID NO: 4.

5. An isolated polypeptide consisting of the amino acid sequence of SEQ ID NO: 5.

* * * * *

SEQUENCE LISTING

```
<160> NUMBER OF SEQ ID NOS: 10

<210> SEQ ID NO 1
<211> LENGTH: 840
<212> TYPE: PRT
<213> ORGANISM: Artificial Sequence
<220> FEATURE:
<223> OTHER INFORMATION: Description of Artificial Sequence: Conductine
      protein

<400> SEQUENCE: 1

Met Ser Ser Ala Val Leu Val Thr Leu Leu Pro Asp Pro Ser Ser Ser
 1               5                  10                  15

Phe Arg Glu Asp Ala Pro Arg Pro Val Pro Gly Glu Glu Gly Glu
            20                  25                  30
```

-continued

```
Thr Pro Pro Cys Gln Pro Ser Val Gly Lys Val Gln Ser Thr Lys Pro
        35                  40                  45

Met Pro Val Ser Ser Asn Ala Arg Arg Asn Glu Asp Gly Leu Gly Glu
    50                  55                  60

Pro Glu Gly Arg Ala Ser Pro Asp Ser Pro Leu Thr Arg Trp Thr Lys
65                  70                  75                  80

Ser Leu His Ser Leu Leu Gly Asp Gln Asp Gly Ala Tyr Leu Phe Arg
                85                  90                  95

Thr Phe Leu Glu Arg Glu Lys Cys Val Asp Thr Leu Asp Phe Trp Phe
            100                 105                 110

Ala Cys Asn Gly Phe Arg Gln Met Asn Leu Lys Asp Thr Lys Thr Leu
        115                 120                 125

Arg Val Ala Lys Ala Ile Tyr Lys Arg Tyr Ile Glu Asn Asn Ser Val
    130                 135                 140

Val Ser Lys Gln Leu Lys Pro Ala Thr Lys Thr Tyr Ile Arg Asp Gly
145                 150                 155                 160

Ile Lys Lys Gln Gln Ile Gly Ser Val Met Phe Asp Gln Ala Gln Thr
                165                 170                 175

Glu Ile Gln Ala Val Met Glu Glu Asn Ala Tyr Gln Val Phe Leu Thr
            180                 185                 190

Ser Asp Ile Tyr Leu Glu Tyr Val Arg Ser Gly Gly Glu Asn Thr Ala
        195                 200                 205

Tyr Met Ser Asn Gly Gly Leu Gly Ser Leu Lys Val Leu Cys Gly Tyr
    210                 215                 220

Leu Pro Thr Leu Asn Glu Glu Glu Trp Thr Cys Ala Asp Leu Lys
225                 230                 235                 240

Cys Lys Leu Ser Pro Thr Val Val Gly Leu Ser Ser Lys Thr Leu Arg
                245                 250                 255

Ala Thr Ala Ser Val Arg Ser Thr Glu Thr Ala Glu Asn Gly Phe Arg
            260                 265                 270

Ser Phe Lys Arg Ser Asp Pro Val Asn Pro Tyr His Val Gly Ser Gly
        275                 280                 285

Tyr Val Phe Ala Pro Ala Thr Ser Ala Asn Asp Ser Glu Leu Ser Ser
    290                 295                 300

Asp Ala Leu Thr Asp Ser Met Ser Met Thr Asp Ser Ser Val Asp
305                 310                 315                 320

Gly Val Pro Pro Tyr Arg Met Gly Ser Lys Lys Gln Leu Gln Arg Glu
                325                 330                 335

Met His Arg Ser Val Lys Ala Asn Gly Gln Val Ser Leu Pro His Phe
            340                 345                 350

Pro Arg Thr His Arg Leu Pro Lys Glu Met Thr Pro Val Glu Pro Ala
        355                 360                 365

Ala Phe Ala Ala Glu Leu Ile Ser Arg Leu Glu Lys Leu Lys Leu Glu
    370                 375                 380

Leu Glu Ser Arg His Ser Leu Glu Glu Arg Leu Gln Gln Ile Arg Glu
385                 390                 395                 400

Asp Glu Glu Lys Glu Gly Ser Glu Gln Ala Leu Ser Ser Arg Asp Gly
                405                 410                 415

Ala Pro Val Gln His Pro Leu Ala Leu Pro Ser Gly Ser Tyr Glu
            420                 425                 430

Glu Asp Pro Gln Thr Ile Leu Asp Asp His Leu Ser Arg Val Leu Lys
        435                 440                 445
```

-continued

```
Thr Pro Gly Cys Gln Ser Pro Gly Val Gly Arg Tyr Ser Pro Arg Ser
    450                 455                 460
Arg Ser Pro Asp His His His Gln His His His Gln Gln Cys His
465                 470                 475                 480
Thr Leu Leu Ser Thr Gly Gly Lys Leu Pro Pro Val Ala Ala Cys Pro
                485                 490                 495
Leu Leu Gly Gly Lys Ser Phe Leu Thr Lys Gln Thr Thr Lys His Val
            500                 505                 510
His His His Tyr Ile His His His Ala Val Pro Lys Thr Lys Glu Glu
        515                 520                 525
Ile Glu Ala Glu Ala Thr Gln Arg Val Arg Cys Leu Cys Pro Gly Gly
    530                 535                 540
Thr Asp Tyr Tyr Cys Tyr Ser Lys Cys Lys Ser His Pro Lys Ala Pro
545                 550                 555                 560
Glu Pro Leu Pro Gly Glu Gln Phe Cys Gly Ser Arg Gly Gly Thr Leu
                565                 570                 575
Pro Lys Arg Asn Ala Lys Gly Thr Glu Pro Gly Leu Ala Leu Ser Ala
            580                 585                 590
Arg Asp Gly Gly Met Ser Ser Ala Ala Gly Gly Pro Gln Leu Pro Gly
        595                 600                 605
Glu Glu Gly Asp Arg Ser Gln Asp Val Trp Gln Trp Met Leu Glu Ser
    610                 615                 620
Glu Arg Gln Ser Lys Ser Lys Pro His Ser Ala Gln Ser Ile Arg Lys
625                 630                 635                 640
Ser Tyr Pro Leu Glu Ser Ala Arg Ala Ala Pro Gly Glu Arg Val Ser
                645                 650                 655
Arg His His Leu Leu Gly Ala Ser Gly His Ser Arg Ser Val Ala Arg
            660                 665                 670
Ala His Pro Phe Thr Gln Asp Pro Ala Met Pro Pro Leu Thr Pro Pro
        675                 680                 685
Asn Thr Leu Ala Gln Leu Glu Glu Ala Cys Arg Arg Leu Ala Glu Val
    690                 695                 700
Ser Lys Pro Gln Lys Gln Arg Cys Cys Val Ala Ser Gln Gln Arg Asp
705                 710                 715                 720
Arg Asn His Ser Ala Ala Gly Gln Ala Gly Ala Ser Pro Phe Ala Asn
                725                 730                 735
Pro Ser Leu Ala Pro Glu Asp His Lys Glu Pro Lys Lys Leu Ala Ser
            740                 745                 750
Val His Ala Leu Gln Ala Ser Glu Leu Val Val Thr Tyr Phe Phe Cys
        755                 760                 765
Gly Glu Glu Ile Pro Tyr Arg Arg Met Leu Lys Ala Gln Ser Leu Thr
    770                 775                 780
Leu Gly His Phe Lys Glu Gln Leu Ser Lys Lys Gly Asn Tyr Arg Tyr
785                 790                 795                 800
Tyr Phe Lys Lys Ala Ser Asp Glu Phe Ala Cys Gly Ala Val Phe Glu
                805                 810                 815
Glu Ile Trp Asp Asp Glu Thr Val Leu Pro Met Tyr Glu Gly Arg Ile
            820                 825                 830
Leu Gly Lys Val Glu Arg Ile Asp
        835                 840

<210> SEQ ID NO 2
<211> LENGTH: 123
<212> TYPE: PRT
```

<213> ORGANISM: Artificial Sequence
<220> FEATURE:
<223> OTHER INFORMATION: Description of Artificial Sequence: Partial
      sequence of conductin protein 78-200 (rgs-domain)

<400> SEQUENCE: 2

Trp Thr Lys Ser Leu His Ser Leu Leu Gly Asp Gln Asp Gly Ala Tyr
 1               5                  10                  15

Leu Phe Arg Thr Phe Leu Glu Arg Glu Lys Cys Val Asp Thr Leu Asp
             20                  25                  30

Phe Trp Phe Ala Cys Asn Gly Phe Arg Gln Met Asn Leu Lys Asp Thr
         35                  40                  45

Lys Thr Leu Arg Val Ala Lys Ala Ile Tyr Lys Arg Tyr Ile Glu Asn
     50                  55                  60

Asn Ser Val Val Ser Lys Gln Leu Lys Pro Ala Thr Lys Thr Tyr Ile
 65                  70                  75                  80

Arg Asp Gly Ile Lys Lys Gln Ile Gly Ser Val Met Phe Asp Gln
                 85                  90                  95

Ala Gln Thr Glu Ile Gln Ala Val Met Glu Glu Asn Ala Tyr Gln Val
            100                 105                 110

Phe Leu Thr Ser Asp Ile Tyr Leu Glu Tyr Val
            115                 120

<210> SEQ ID NO 3
<211> LENGTH: 54
<212> TYPE: PRT
<213> ORGANISM: Artificial Sequence
<220> FEATURE:
<223> OTHER INFORMATION: Description of Artificial Sequence: Partial
      sequence of conductin protein 343-396 (GSK 3)

<400> SEQUENCE: 3

Ala Asn Gly Gln Val Ser Leu Pro His Phe Pro Arg Thr His Arg Leu
 1               5                  10                  15

Pro Lys Glu Met Thr Pro Val Glu Pro Ala Ala Phe Ala Ala Glu Leu
             20                  25                  30

Ile Ser Arg Leu Glu Lys Leu Lys Leu Glu Leu Glu Ser Arg His Ser
         35                  40                  45

Leu Glu Glu Arg Leu Gln
     50

<210> SEQ ID NO 4
<211> LENGTH: 69
<212> TYPE: PRT
<213> ORGANISM: Artificial Sequence
<220> FEATURE:
<223> OTHER INFORMATION: Description of Artificial Sequence: Partial
      sequence of conductin protein 397-465 (-catenine
      binding domain)

<400> SEQUENCE: 4

Gln Ile Arg Glu Asp Glu Glu Lys Glu Gly Ser Glu Gln Ala Leu Ser
 1               5                  10                  15

Ser Arg Asp Gly Ala Pro Val Gln His Pro Leu Ala Leu Leu Pro Ser
             20                  25                  30

Gly Ser Tyr Glu Glu Asp Pro Gln Thr Ile Leu Asp Asp His Leu Ser
         35                  40                  45

Arg Val Leu Lys Thr Pro Gly Cys Gln Ser Pro Gly Val Gly Arg Tyr
     50                  55                  60

```
Ser Pro Arg Ser Arg
 65
```

<210> SEQ ID NO 5
<211> LENGTH: 51
<212> TYPE: PRT
<213> ORGANISM: Artificial Sequence
<220> FEATURE:
<223> OTHER INFORMATION: Description of Artificial Sequence: Partial
    sequence of conductin protein 783-833 (dishevelled
    homologe region)

<400> SEQUENCE: 5

```
Leu Thr Leu Gly His Phe Lys Glu Gln Leu Ser Lys Lys Gly Asn Tyr
 1               5                  10                  15

Arg Tyr Tyr Phe Lys Lys Ala Ser Asp Glu Phe Ala Cys Gly Ala Val
            20                  25                  30

Phe Glu Glu Ile Trp Asp Asp Glu Thr Val Leu Pro Met Tyr Glu Gly
        35                  40                  45

Arg Ile Leu
     50
```

<210> SEQ ID NO 6
<211> LENGTH: 2825
<212> TYPE: DNA
<213> ORGANISM: Artificial Sequence
<220> FEATURE:
<223> OTHER INFORMATION: Description of Artificial Sequence: cDNA of
    conductine protein

<400> SEQUENCE: 6

| | | | | | |
|---|---|---|---|---|---|
| cagccgttcg | cgatggattt | cggggccacc | cggaggccga | ggcgtccggc | tccccaaagg | 60 |
| agagctttgc | tgtaaaagag | aggaggctca | catgagcccc | tgctgactta | agagagacca | 120 |
| agccgattgc | tgagaggaac | tggaagaaga | aaaggagga | ggagggaaaa | aaagcaaaac | 180 |
| aaaatccaaa | ctcagtgaga | cgctctccct | caccatgagt | agcgccgtgt | tagtgactct | 240 |
| ccttccagat | cccagcagca | gcttccgcga | ggatgctccg | cggcccccgg | ttccgggaga | 300 |
| agaaggggag | accccaccgt | gtcagcctag | tgtgggcaag | gtccagtcca | ccaaacctat | 360 |
| gcccgttttcc | tctaatgcta | ggcggaatga | agatggactg | ggggagcccg | aggggcgggc | 420 |
| ctccccccgat | tcccctttga | ccaggtggac | caagtctttta | cactccttgt | tgggtgacca | 480 |
| ggatggtgca | tacctcttcc | ggactttcct | ggagagggga | aatgtgtgg | atacgctgga | 540 |
| cttctggtttt | gcttgtaatg | ggttcaggca | gatgaacctg | aaggatacca | aactttgcg | 600 |
| agtggccaaa | gcaatctata | agaggtacat | tgagaacaac | agcgttgtct | ccaagcagct | 660 |
| gaagcccgcc | accaagacct | acatacgaga | tggcatcaag | aagcaacaga | tcggctcggt | 720 |
| catgtttgac | caggcacaga | ccgagatcca | ggcagtgatg | gaggaaaatg | cctaccaggt | 780 |
| gttcttgact | tctgacattt | acctggaata | tgtgaggagt | gggggggaaa | acacagctta | 840 |
| catgagtaac | gggggactgg | ggagcctaaa | ggtcttatgt | ggctacctcc | ccaccttgaa | 900 |
| tgaagaagag | gagtggacgt | gtgccgacct | caagtgcaaa | ctctcaccca | ccgtggttgg | 960 |
| cttgtccagc | aaaactcttc | gggccaccgc | gagtgtgaga | tccacggaaa | cagctgaaaa | 1020 |
| cggattcagg | tccttcaaga | gaagcgaccc | agtcaatcct | tatcacgtag | gttccggcta | 1080 |
| tgtctttgca | ccagccacca | gcgccaacga | cagcgagtta | tccagcgacg | cactgaccga | 1140 |
| cgattccatg | tccatgacgg | acagtagcgt | agatggagtc | cctccttacc | gcatggggag | 1200 |

```
taagaaacag ctccagagag agatgcatcg cagtgtgaag gccaatggcc aagtgtctct   1260
acctcatttt ccgagaaccc accgcctgcc caaggagatg acgcctgtgg aacctgctgc   1320
cttcgccgcc gagctcatct ccaggctgga gaaactgaaa ctggagctgg aaagccgcca   1380
tagtctggag gagcggctgc agcagatccg ggaggatgaa gaaaaggagg ggtctgagca   1440
ggccctgagc tcacgggatg gagcaccggt ccagcacccc ctggccctcc taccctccgg   1500
cagctatgaa gaggacccac aaaccatttt ggacgaccac ctctccaggg tcctcaagac   1560
ccccggctgt caatcccctg gtgtgggtcg ctacagccca cggtcccgct ccccgacca   1620 ccaccaccag caccaccacc atcagcagtg tcataccctt ctttcgactg ggggcaagct   1680 gcccccgtg gctgcttgcc ccctccttgg aggcaagagc ttcctgacca aacagacgac   1740
gaagcacgtt caccaccact acatccacca ccacgccgtc cccaagacca aggaggagat   1800
cgaggcagaa gccacacaga gagtccgctg cctctgtcct gggggaacag attattattg   1860
ctactccaaa tgcaaaagcc acccgaaggc tccagagccc ctgcctgggg agcagttttg   1920
tggcagcaga ggtggtacct tgccaaaacg gaatgcaaag ggcaccgaac cgggtcttgc   1980
actgtcggcc agggatggag ggatgtccag tgcagcgggg ggcccccagc ttcctgggga   2040
agaaggagac cggtcacagg atgtctggca gtggatgttg gagagtgagc ggcagagcaa   2100
gtccaagccc catagtgccc aaagcataag aaagagctac ccattggagt ctgcccgtgc   2160
ggccccagga gaacgagtca gccggcacca tctgttgggg gccagcggac actcccgctc   2220
agtggcccgg gctcacccat ttacccagga ccctgcaatg cctcccctta ccccaccaa   2280 cactttggca cagctagagg aagcctgccg caggctggca gaggtgtcga agccccagaa   2340
gcagcggtgc tgcgtggcca gtcagcgagg ggacaggaac cactcggctg ctggtcaggc   2400
aggagcctca cccttcgcca acccaagcct ggctccagaa gatcacaaag agccaaagaa   2460
actggcaagt gtccacgcgc tccaggccag tgagctggtt gtcacctact ttttctgtgg   2520
agaagaaatt ccatacagga ggatgctgaa ggctcaaagc ttgaccctgg gccacttcaa   2580
ggagcagctc agcaaaaagg gaaattacag gtattatttc aagaaggcga gtgacgaatt   2640
tgcctgcgga gcagtttttg aggagatctg ggacgacgag acagtgctcc ccatgtacga   2700
aggcaggatc ctgggcaaag tggagaggat cgactgagcc ttggcctcct cggcgtgcaa   2760
cctgggcaag cacctcggcg tgcaccatgg agccgaagcc cagagaccct gtctcaggcc   2820
tacgc                                                               2825
```

<210> SEQ ID NO 7
<211> LENGTH: 369
<212> TYPE: DNA
<213> ORGANISM: Artificial Sequence
<220> FEATURE:
<223> OTHER INFORMATION: Description of Artificial Sequence: cDNA
    partial sequence 446-814

<400> SEQUENCE: 7

```
tggaccaagt ctttacactc cttgttgggt gaccaggatg gtgcatacct cttccggact     60
ttcctggaga gggagaaatg tgtggatacg ctggacttct ggtttgcttg taatgggttc    120
aggcagatga acctgaagga taccaaaact ttgcgagtgg ccaaagcaat ctataagagg    180
tacattgaga acaacagcgt tgtctccaag cagctgaagc ccgccaccaa gacctacata    240
cgagatggca tcaagaagca acagatcggc tcggtcatgt tgaccaggc acagaccgag    300 atccaggcag tgatggagga aaatgcctac caggtgttct tgacttctga catttacctg    360
```

```
gaatatgtg                                                              369
```

<210> SEQ ID NO 8
<211> LENGTH: 162
<212> TYPE: DNA
<213> ORGANISM: Artificial Sequence
<220> FEATURE:
<223> OTHER INFORMATION: Description of Artificial Sequence: cDNA
      partial sequence 1241-1402

<400> SEQUENCE: 8

```
gccaatggcc aagtgtctct acctcatttt ccgagaaccc accgcctgcc caaggagatg    60
acgcctgtgg aacctgctgc cttcgccgcc gagctcatct ccaggctgga gaaactgaaa   120
ctggagctgg aaagccgcca tagtctggag gagcggctgc ag                      162
```

<210> SEQ ID NO 9
<211> LENGTH: 207
<212> TYPE: DNA
<213> ORGANISM: Artificial Sequence
<220> FEATURE:
<223> OTHER INFORMATION: Description of Artificial Sequence: cDNA
      partial sequence 1403-1609

<400> SEQUENCE: 9

```
cagatccggg aggatgaaga aaaggagggg tctgagcagg ccctgagctc acgggatgga    60
gcaccggtcc agcacccct  ggccctccta ccctccggca gctatgaaga ggacccacaa   120
accattttgg acgaccacct ctccagggtc ctcaagaccc ccggctgtca atcccctggt   180
gtgggtcgct acagcccacg gtcccgc                                       207
```

<210> SEQ ID NO 10
<211> LENGTH: 153
<212> TYPE: DNA
<213> ORGANISM: Artificial Sequence
<220> FEATURE:
<223> OTHER INFORMATION: Description of Artificial Sequence: cDNA
      partial sequence 2561-2713

<400> SEQUENCE: 10

```
ttgaccctgg gccacttcaa ggagcagctc agcaaaaagg gaaattacag gtattatttc    60
aagaaggcga gtgacgaatt tgcctgcgga gcagtttttg aggagatctg ggacgacgag   120
acagtgctcc ccatgtacga aggcaggatc ctg                                153
```